US011412994B2

(12) United States Patent
Yang

(10) Patent No.: US 11,412,994 B2
(45) Date of Patent: *Aug. 16, 2022

(54) SYSTEM AND METHOD FOR ALGORITHM ADJUSTMENT APPLYING MOTIONS SENSOR IN A CGM SYSTEM

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 482 days.

This patent is subject to a terminal disclaimer.

(21) Appl. No.: 16/470,559

(22) PCT Filed: Dec. 30, 2016

(86) PCT No.: PCT/CN2016/113676
§ 371 (c)(1),
(2) Date: Jun. 18, 2019

(87) PCT Pub. No.: WO2018/120096
PCT Pub. Date: Jul. 5, 2018

(65) Prior Publication Data
US 2019/0328340 A1    Oct. 31, 2019

(51) Int. Cl.
*A61B 5/00* (2006.01)
*A61B 5/11* (2006.01)
*A61B 5/145* (2006.01)

(52) U.S. Cl.
CPC ............ *A61B 5/746* (2013.01); *A61B 5/1118* (2013.01); *A61B 5/14532* (2013.01);
(Continued)

(58) Field of Classification Search
CPC ... A61B 5/746; A61B 5/1118; A61B 5/14532; A61B 5/7225; A61B 5/7405;
(Continued)

(56) References Cited

U.S. PATENT DOCUMENTS

2004/0152958 A1    8/2004   Frei et al.
2006/0241708 A1    10/2006  Boute
(Continued)

OTHER PUBLICATIONS

Sobel et al., Accuracy of a Novel Noninvasive Multisensor Technology to Estimate Glucose in Diabetic Subjects During Dynamic Conditions, 2014, Journal of Diabetes Science and Technology, vol. 8(I), pp. 54-63 (Year: 2014).*

(Continued)

*Primary Examiner* — Toan M Le
(74) *Attorney, Agent, or Firm* — JCIP Global Inc.

(57) ABSTRACT

A method for algorithm adjustment applying a motion sensor in a Continuous Glucose Monitoring system and a system using the method are provided. The method includes sensing an activity level of a patient by a motion sensor set in a CGM device of the CGM system and providing signals to a processer, then adjusting a series of related algorithms depending partly on the signals by the processer to provide more accurate and reliable blood glucose related data that is the basis of desirable treatment plans, and automatically operating the COM device including switching the CGM device to an audio-off mode or pausing a calibration of the glucose sensor by the processer.

9 Claims, 4 Drawing Sheets

(52) U.S. Cl.
CPC .......... *A61B 5/7225* (2013.01); *A61B 5/7405* (2013.01); *A61B 2560/0223* (2013.01); *A61B 2562/0219* (2013.01)

(58) Field of Classification Search
CPC ... A61B 5/14503; A61B 5/1495; A61B 5/725; A61B 5/0022; A61B 2560/0223; A61B 2562/0219; G16H 40/67; G06H 50/20
See application file for complete search history.

(56) References Cited

U.S. PATENT DOCUMENTS

2010/0113895 A1    5/2010    Cho et al.
2010/0121215 A1    5/2010    Giftakis et al.
2019/0307958 A1*  10/2019  Yang .................... A61B 5/1118

OTHER PUBLICATIONS

"International Search Report (Form PCT/ISA/210) of PCT/CN2016/113676," dated Sep. 6, 2017, pp. 1-2.

* cited by examiner

SYSTEM AND METHOD FOR ALGORITHM ADJUSTMENT APPLYING MOTIONS SENSOR IN A CGM SYSTEM

CROSS-REFERENCE TO RELATED APPLICATION

This application is a 371 of international application of PCT application serial no. PCT/CN2016/113676, filed on Dec. 30, 2016. The entirety of the above-mentioned patent application is hereby incorporated by reference herein and made a part of this specification.

TECHNICAL FIELD

This invention generally relates to medical appliance, and more specifically to a system and method for algorithm adjustment applying motion sensors in a CGM system.

BACKGROUND

For a normal healthy person, the pancreas produces and releases insulin into the blood stream in response to elevated blood glucose levels. βcells, which reside in the pancreas, produce and secrete the insulin into the blood stream, as it is needed. If βcells become incapacitated or die, a condition known as Type I diabetes mellitus, or in some cases if βcells produce insufficient quantities of insulin, Type II diabetes, then insulin must be provided to the body of the patient from another source.

Traditionally, since insulin cannot be taken orally, insulin has been injected with a syringe. More recently, use of infusion pump therapy has been increasing, especially for delivering insulin for diabetics. For example, external infusion pumps are worn on a belt, in a pocket, or patched to the body of the patient directly, and deliver insulin into the body by an infusion tube with a percutaneous needle or a cannula placed in the subcutaneous tissue. The medicine that is delivered by the infusion pump device can depend on the condition of the patient and the desired treatment plan. However, current insulin pumps and other diabetes treatment instruments are limited in switching between different treatment plans based on different conditions of the patient.

Desired treatment plans depend on accurate determination of different conditions of the patient, especially for the continuously glucose monitoring in tissue fluid whose concentration is easily influenced by the actions of the patient. If a patient is in sleep, due to less activity taking place in the muscle and organs than the normal state, whether she or he being in a state of low blood glucose needs to be recalculated by an adjusted algorithm. Furthermore, some low-priority alerts should be muted to prevent disturbing the patient from sleep. Similarly, if a patient is doing physical exercise, her or his blood glucose value may fluctuate sharply, but her or his blood glucose level should not be determined as abnormal, and this false "abnormal fluctuations" of the blood glucoses level should be excluded. In pursuing desirable treatment plans, the combination of sensing the activity level of the patient and adjusting the blood glucose related algorithms to provide more accurate data became crucial.

SUMMARY OF THE INVENTION

To overcome the deficiencies of the prior art, one purpose of the present invention is to provide a method for adjusting blood glucose related algorithms in a continuous glucose monitoring (CGM) system, comprising, sensing an activity level of a patient by at least one motion sensor and providing signals indicative of the activity level to a processer in the CGM system;

determining the physical state of the patient according to the activity level and adjusting a plurality of algorithms via the processer depending partly on the signals from the motion sensor when the patient is determined in a sleep or physical exercise state.

Alternatively, the motion sensor comprises one or more from an accelerometer, a gyroscope and an attitude sensor.

Alternatively, the method further comprises adjusting the algorithms according to different exercise intensities when the patient is in a state of physical exercise.

Alternatively, the blood glucose related algorithms comprise but not limited to a filtering algorithm configured to calculate the blood glucose value, a predictive low glucose algorithm and an alert threshold algorithm.

Alternatively, the method further comprises automatically switch the CGM system into an audio-off mode for low-priority alerts that do not require immediate action according to the adjusted algorithm.

Alternatively, the method further comprises excluding abnormal fluctuations of the blood glucose sensor data by adjusting related algorithms via the processer when the patient is determined in a state of physical exercise via the processer.

Alternatively, when a calibration of the blood glucose sensor is performed at the same time of an abnormal fluctuation taking place, related algorithm is adjusted via the processer to pause the calibration until the abnormal fluctuation is excluded.

The other purpose of the present invention is to provide a system using the method for adjusting blood glucose related algorithms identified above, comprising a CGM system with a processer and at least one motion sensor set in the CGM system.

The motion sensor is configured to sense the activity levels of a patient and provide corresponding signals; and the processer is configured to determine the physiological states and exercise intensities of the patient and adjust blood glucose related algorithms depending partly on the signals from the motion sensor.

The glucose data processed by the processer using the adjusted algorithm might be sent to a handset or a smart device to display or be further processed to control a patch pump.

The present invention has advantages in the following ways: Firstly, applying the motion sensor in the CGM system enables a comprehensive grasp of the patient's activity levels for a more rational treatment by distinguishing sleep and physical exercise states from the normal state, adjusting blood glucose related algorithms according to different activity levels and exercise intensities of the patient provides more reliable data that leads directly to appropriate treatments. Secondly, because the continuously glucose monitoring system detects the glucose level in tissue fluid which is easily influenced by the attitude and activity level of a subject, excluding abnormal fluctuation of the sensor glucose level better reflects the real situation of the patient. Thirdly, muting some low-priority alerts when the patient is determined in the state of sleep or exercise reduces unnecessary disturbance to the patient, making the system more pleasant to use. To sum up, the application of motion sensor in the CGM system enables algorithm adjustments based on different physical states and exercise intensities of the patient to provide more accurate and reliable blood glucose related data that is the basis of desirable treatment plans, and a CGM system using this method satisfies the requirements of the patient on safety and intelligence of a glucose monitoring device in a more sophisticated way.

DETAILED DESCRIPTION

To make the above-mentioned objects, features and advantages of the present invention more obvious and understandable, the embodiments of the present invention are described in the following through specific embodiments.

Figure 1:
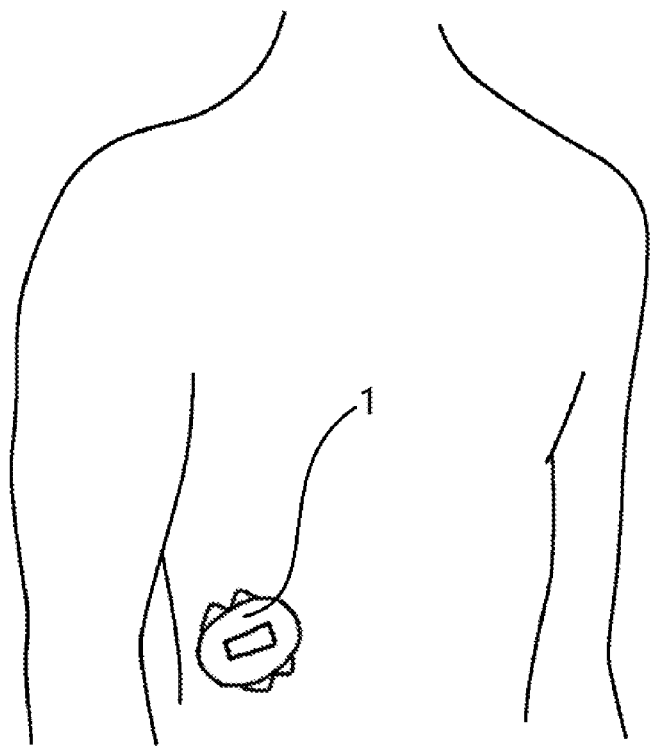
FIG. 1 is a schematic diagram of a patient wearing a CGM system in the present invention.
Figure 2:
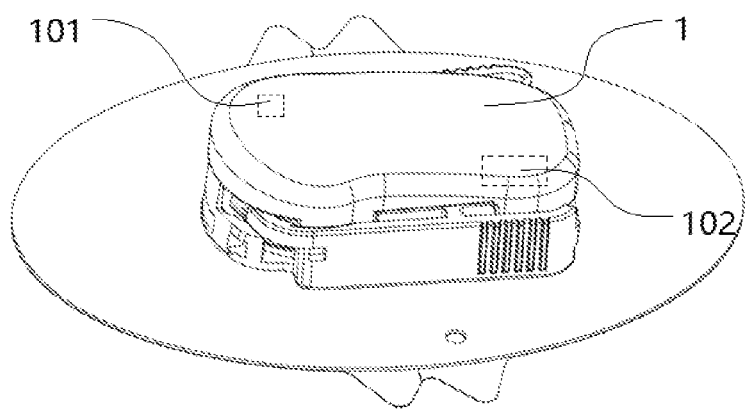
FIG. 2 is a schematic diagram of the CGM system in the present invention.

Referring to FIG. 1 and FIG. 2, an embodiment of the present invention is provided. FIG. 1 illustrates a patient wearing a CGM system 1 configured to monitor the blood glucose changes of the patient in real time. FIG. 2 illustrates the structure of the CGM system 1, comprising a motion sensor 101 and a processor 102.

As shown in FIG. 2, a motion sensor 101 is set in the CGM system 1, configured to sense activity levels of the patient and send corresponding signals to the processor 102. In this embodiment, the motion sensor 101 is a three-axis accelerometer 101, sensing the activity levels and state changes of the patient in three axes, and the processor 102 receives signals from the three-axis accelerometer 101 and adjusts corresponding algorithms depending partly on the signals.

When the patient is in physical exercise, the start and end of the exercise, as well as the intensity of the exercise can be determined by the equation:

$$ACC_{power} = \sqrt{ACC_X^2 + ACC_Y^2 + ACC_Z^2}$$

Where, $ACC_{power}$ is the acceleration amplitude of all three axes;
$ACC_X$ is the acceleration data of the X axis;
$ACC_Y$ is the acceleration data of the Y axis;
$ACC_Z$ is the acceleration data of the Z axis.

The attitudes of the patient, whether she or he is standing, sitting, lying, or changing from one of these attitudes to another, can be sensed by the three-axis accelerometer 101. In other words, the attitude changes of the patient can be tracked by the three-axis accelerometer 101 in real time. When the patient goes to sleep, the state can be determined by the equation:

$$ACC_{var} = (ACC_X - ACC_{X|PRE})^2 + (ACC_Y - ACC_{Y|PRE})^2 + ((ACC_Z - ACC_{Z|PRE})^2$$

Where, $ACC_{var}$ is the acceleration variation of all three axes;
$ACC_X$ is the acceleration data of the X axis;
$ACC_Y$ is the acceleration data of the Y axis;
$ACC_Z$ is the acceleration data of the Z axis;
$ACC_{X|PRE}$ is the acceleration data of the X axis at a previous time;
$ACC_{Y|PRE}$ is the acceleration data of the Y axis at a previous time;
$ACC_{Z|PRE}$ is the acceleration data of the Z axis at a previous time.

Figure 3:
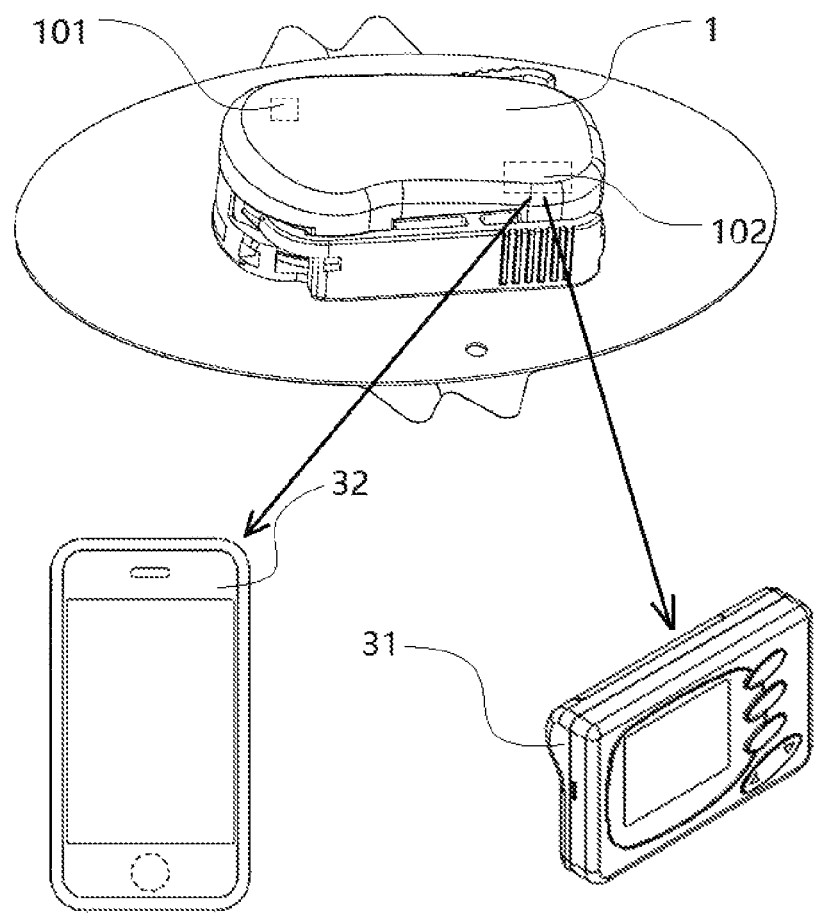
FIG. 3 is a schematic diagram of the representative method in an embodiment of the present invention.

Referring to FIG. 3, an embodiment of the present invention is provided. As shown in FIG. 3, a motion sensor 101 is set in the CGM system 1 to sense activity levels of the patient and send corresponding signals. A processer 102 set in the CGM system 1 receives signals from the motion sensor 101 and adjusts related algorithms depending partly on the signals, and the data processed using the adjusted algorithms is sent to a handset 31 or a smart phone 32 to display.

Figure 4:
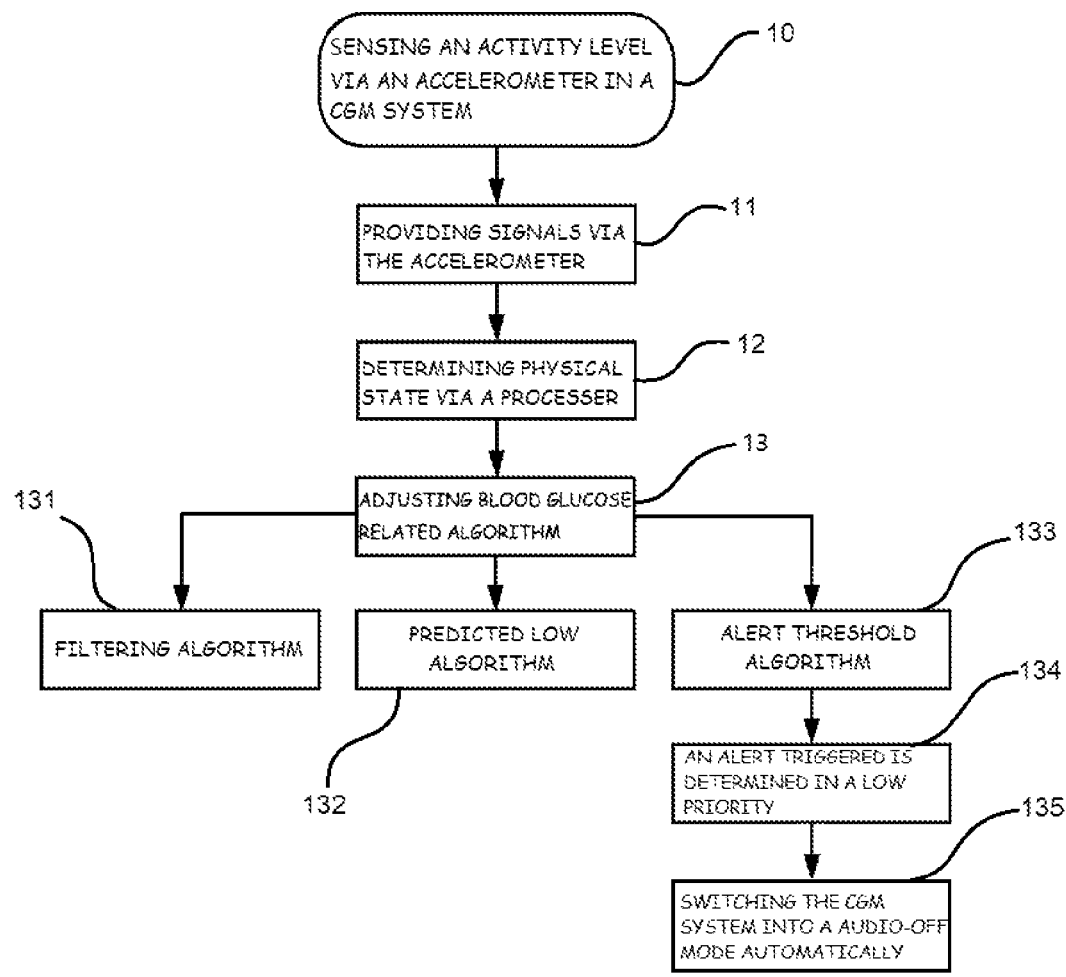
FIG. 4 is a flow chart of the representative method in an embodiment of the present invention.

FIG. 4 is a flow chart of an exemplary method illustrating the co-operation of the accelerometer and the processer set in the CGM system. When a patient goes to sleep or physical exercise, her or his change of state can be sensed by an accelerometer or an attitude sensor, in this embodiment, an accelerometer set in the CGM system. At block 10, the accelerometer senses an activity level of the patient. At block 11, the accelerometer provides signals indicative of the activity level to a processor in the CGM system. At block 12, the processer in the CGM system determines whether the patient is in a sleep or physical exercise state according to the signals from the accelerometer. At block 13, the processer adjusts a series of related algorithms depending partly on the signals from the accelerometer, including but not limited to a filtering algorithm to calculate the blood glucose value as illustrated at block 131, a predictive low glucose algorithm as illustrated at block 132, and an alert threshold algorithm as illustrated at block 133. At block 134, when an alert is determined to be low priority according to the adjusted alert threshold calculating algorithm, the processor will automatically switch the CGM system into an audio-off mode as illustrated at block 135, avoiding disturbing the patient in her or his normal sleep or normal exercise.

Figure 5:
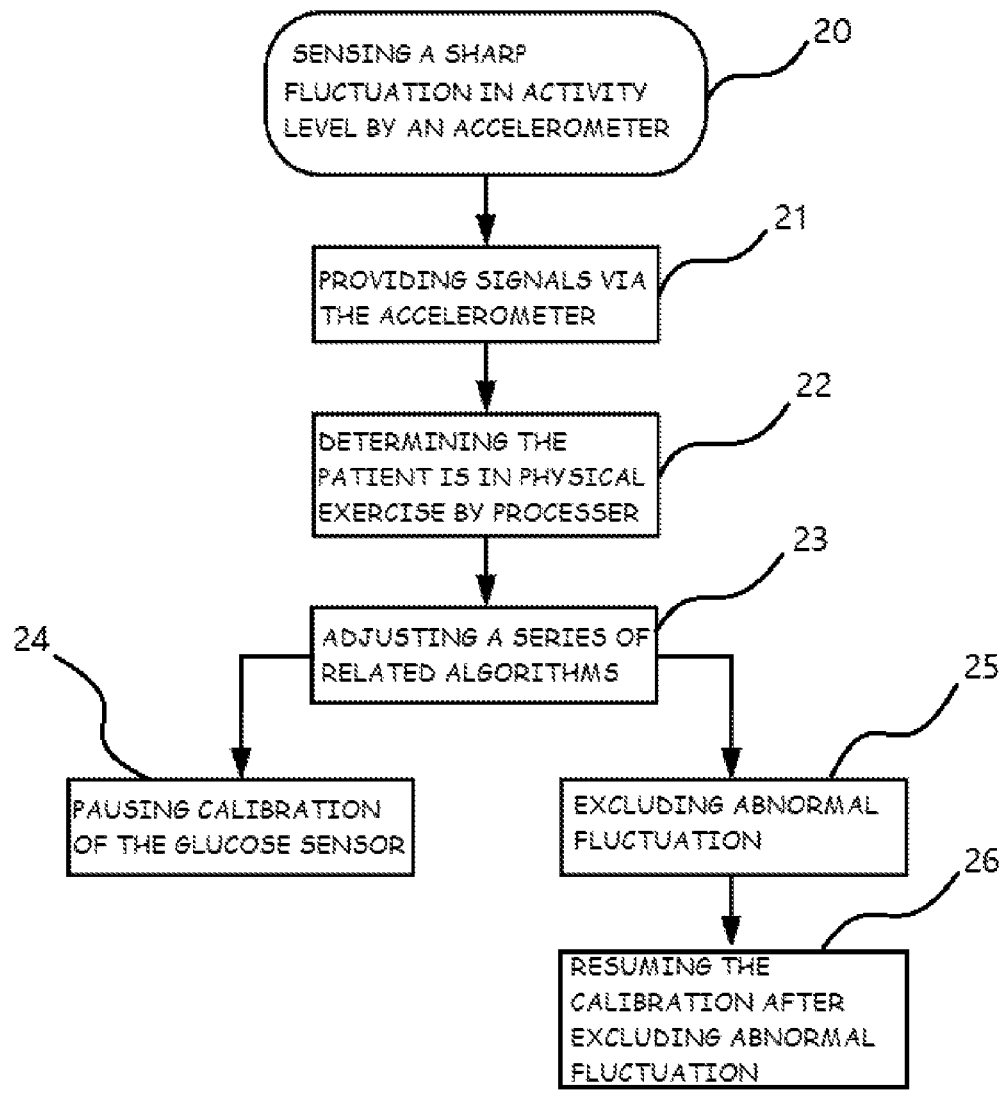
FIG. 5 is a flow chart of the representative method in an embodiment of the present invention.

FIG. 5 is a flow chart of an exemplary method illustrating the co-operation of the motion sensor and the processer when the patient is in the state of physical exercise. When the patient is doing physical exercise, the concentration of her or his tissue fluid may go through instant dramatic changes because of squeezing and stretching actions, so her or his glucose level sensed by a glucose sensor may fluctuate sharply but should not be determined as abnormal. At block 20, an accelerometer senses a sharp fluctuation in activity level of the patient. At block 21, the accelerometer provides signals indicative of the activity level to the processer in the CGM system. At block 22, the processer in the CGM system determines the patient is in a physical exercise state according to the signals from the accelerometer. At block 23, the processor adjusts a series of algorithms depending partly on the signals from the accelerometer. At block 24, the processer forbids a calibration of the glucose sensor for the reason that the calibration result would be unreliable during a fast-changing period of the glucose level. At block 25, the processor excludes the abnormal fluctuation using the adjusted algorithm. At block 26, the processor allows the calibration of the glucose sensor when the abnormal fluctuation is excluded.

The above descriptions of the detailed embodiments are only to illustrate the principle and the effect of the present invention, and it is not to limit the scope of the present invention. Those skilled in the art can modify or change the embodiments without departing from the spirit and scope of the present invention. Accordingly, all equivalent modifications and variations completed by persons of ordinary skill in the art, without departing from the spirit and technical idea of the present invention, should fall within the scope of the present disclosure defined by the appended claims.

The invention claimed is:

1. A method for adjusting algorithms in a continuous glucose monitoring (CGM) system, comprising:
   sensing an activity level of a patient by at least one motion sensor set in a CGM device of the CGM system;
   providing signals indicative of the activity level of the patient by the motion sensor to a processor of the CGM device;
   determining the physical state of the patient according to the activity level via the processor;
   adjusting a plurality of algorithms via the processor depending partly on the signals from the motion sensor;
   excluding abnormal fluctuations of the blood glucose sensor data by adjusting related algorithms via the processor when the patient is determined in a state of physical exercise by the processor; and
   transmitting the blood glucose sensor data processed using the adjusted algorithms and/or excluded the abnormal fluctuations by the processor to a portable display device for display.

2. The method according to claim 1, wherein the motion sensor comprises one or more from an accelerometer, a gyroscope and an attitude sensor.

3. The method according to claim 1, wherein further comprises adjusting the algorithms according to different exercise intensities when the patient is in a physical exercise state.

4. The method according to claim 1, wherein the algorithms comprise a filtering algorithm to calculate the blood glucose value.

5. The method according to claim 1, wherein the algorithms comprise a predictive low glucose algorithm.

6. The method according to claim 1, wherein the algorithms comprise an alert threshold algorithm.

7. The method according to claim 6, wherein the method further comprises automatically switching the CGM device into an audio-off mode for low-priority alerts that do not require immediate action according to the adjusted algorithm.

8. The method according to claim 1, wherein when a calibration of the blood glucose sensor is performed at the same time of an abnormal fluctuation taking place, related algorithm is adjusted by the processor to pause the calibration until the abnormal fluctuation is excluded.

9. A system using the method for adjusting blood glucose related algorithms according to claim 1, comprising:
   a CGM device;
   at least one motion sensor set in the CGM device configured to sense the activity levels of a patient and provide corresponding signals; and
   a processor set in the CGM device configured to determine the physiological states and exercise intensities of the patient, adjust related algorithms depending partly on the signals from the motion sensor, and exclude abnormal fluctuations of blood glucose sensor data when the patient is determined in a physical exercise state by the processor,
   wherein the processor is configured to transmit the blood glucose sensor data processed using the adjusted algorithms and/or excluded the abnormal fluctuations to a portable display device for display.

* * * * *